United States Patent
Buell et al.

(10) Patent No.: US 12,258,692 B2
(45) Date of Patent: Mar. 25, 2025

(54) COSMETIC SHEET MASKS FOR IMPROVED PRODUCT DELIVERY

(71) Applicant: ELC Management LLC, Melville, NY (US)

(72) Inventors: Sezen Buell, Harrington Park, NJ (US); Jill Marie Villacci, Merrick, NY (US); Sushil Iyer, Garden City, NY (US); Peter John Tsolis, South Huntington, NY (US)

(73) Assignee: ELC Management LLC, Melville, NY (US)

( * ) Notice: Subject to any disclaimer, the term of this patent is extended or adjusted under 35 U.S.C. 154(b) by 379 days.

(21) Appl. No.: 17/652,996

(22) Filed: Mar. 1, 2022

(65) Prior Publication Data

US 2023/0279590 A1 Sep. 7, 2023

(51) Int. Cl.
| | | |
|---|---|---|
| A61M 35/00 | (2006.01) | |
| A45D 44/00 | (2006.01) | |
| D04H 1/4382 | (2012.01) | |
| D04H 1/492 | (2012.01) | |

(52) U.S. Cl.
CPC ......... *D04H 1/4383* (2020.05); *A45D 44/002* (2013.01); *A61M 35/10* (2019.05); *D04H 1/492* (2013.01); *D10B 2321/021* (2013.01); *D10B 2331/02* (2013.01); *D10B 2331/041* (2013.01); *D10B 2509/00* (2013.01)

(58) Field of Classification Search
CPC ..... D04H 1/4383; D04H 1/492; A61M 35/10; A45D 44/002; D10B 2321/021; D10B 2331/02; D10B 2331/041; D10B 2509/00
See application file for complete search history.

(56) References Cited

U.S. PATENT DOCUMENTS

| | | | | |
|---|---|---|---|---|
| 3,338,992 A * | 8/1967 | Kinney | D01D 5/08 | 264/479 |
| 3,914,365 A * | 10/1975 | Kim | D01D 5/423 | 156/267 |
| 4,340,563 A * | 7/1982 | Appel | B29C 48/87 | 264/237 |
| 4,381,335 A * | 4/1983 | Okamoto | D01D 5/36 | 428/397 |
| 4,551,378 A * | 11/1985 | Carey, Jr. | D04H 1/06 | 156/308.2 |
| 4,612,228 A * | 9/1986 | Kato | D04H 1/43838 | 442/407 |
| 5,045,387 A * | 9/1991 | Schmalz | D06M 15/647 | 428/394 |
| 5,336,552 A * | 8/1994 | Strack | D04H 3/147 | 442/361 |
| 5,470,640 A * | 11/1995 | Modrak | D04H 1/74 | 428/218 |
| 5,582,904 A * | 12/1996 | Harrington | D04H 1/4291 | 442/364 |
| RE35,621 E * | 10/1997 | Schmalz | D06M 15/643 | 252/8.81 |
| 5,721,048 A * | 2/1998 | Schmalz | D04H 1/4291 | 252/8.84 |
| 5,783,503 A * | 7/1998 | Gillespie | D04H 3/16 | 428/394 |
| 5,786,065 A * | 7/1998 | Annis | B24D 11/005 | 428/141 |
| 5,869,010 A * | 2/1999 | Langer | C09K 21/02 | 428/920 |
| 5,889,080 A * | 3/1999 | Kaminski | F16D 69/026 | 525/142 |
| 5,899,785 A * | 5/1999 | Groten | D04H 3/105 | 442/352 |
| 5,916,678 A * | 6/1999 | Jackson | D01F 8/10 | 442/364 |
| 5,919,837 A * | 7/1999 | Kaminski | F16D 69/026 | 525/238 |
| 5,948,528 A * | 9/1999 | Helms, Jr. | D01F 8/12 | 428/397 |
| 5,972,497 A * | 10/1999 | Hirwe | D04H 1/42 | 428/361 |
| 6,110,991 A * | 8/2000 | Kaminski | C08J 5/04 | 523/156 |
| 6,335,092 B1 * | 1/2002 | Takeda | D01F 8/04 | 428/359 |
| 6,448,462 B2 * | 9/2002 | Groitzsch | D04H 3/005 | 602/41 |

(Continued)

FOREIGN PATENT DOCUMENTS

| | | | | |
|---|---|---|---|---|
| KR | 20170002872 A * | 1/2017 | ............ | A45D 44/00 |
| KR | 10-1743916 B1 | 6/2017 | | |

OTHER PUBLICATIONS

PCT International Search Report; International Application No. PCT/US/2023/063079; Completion Date: Jun. 14, 2023; Mailing Date: Jun. 15, 2023; 19.20.

PCT Written Opinion of the International Searching Authority; International Application No. PCT/US2023/063079; Completion Date: Jun. 14, 2023; 19.20.

Behnam Pourdeyhimi; Comments on the Paper Entitled "Splitting of Islands-in-the-Sea Fibers (PA6/COPET) During Hydroentangling of Nonwovens" Journal of Engineered Fibers and Fabrics; vol. 3, Issue 1-2008; pp. 32-35.

*Primary Examiner* — Guy K Townsend

(74) *Attorney, Agent, or Firm* — Peter Giancana

(57) ABSTRACT

Nonwoven fabrics may be fashioned as topical delivery systems with increased and controllable rate of product release, while still possessing the requisite strength and durability for mass production and distribution. Such delivery systems comprise fabrics that are fashioned from microdenier fibers that are produced by fibrillating bicomponent island-in-the-sea fibers. Facial masks made from these fabrics can achieve adequate product delivery in 3-5 minutes or less.

7 Claims, No Drawings

(56) References Cited

U.S. PATENT DOCUMENTS

| | | | | |
|---|---|---|---|---|
| 6,455,156 B2* | 9/2002 | Tanaka | D01D 5/24 | 428/398 |
| 6,468,651 B2* | 10/2002 | Aikawa | D04H 1/4383 | 428/364 |
| 6,506,873 B1* | 1/2003 | Ryan | D04H 1/4291 | 442/364 |
| 6,632,313 B2* | 10/2003 | Nickel | D04H 3/016 | 264/168 |
| 7,291,300 B2* | 11/2007 | Chhabra | D01D 5/423 | 264/122 |
| 7,883,772 B2* | 2/2011 | Pourdeyhimi | D04H 3/16 | 428/401 |
| 7,981,226 B2* | 7/2011 | Pourdeyhimi | D04H 3/16 | 156/62.4 |
| 7,981,336 B2* | 7/2011 | Pourdeyhimi | D01D 5/36 | 264/103 |
| 8,349,232 B2* | 1/2013 | Pourdeyhimi | D04H 1/541 | 28/103 |
| 8,420,556 B2* | 4/2013 | Pourdeyhimi | D01D 5/34 | 442/364 |
| 9,284,663 B2* | 3/2016 | Pourdeyhimi | D01D 5/253 | |
| 9,481,144 B1* | 11/2016 | Duggal | B64D 25/14 | |
| 9,797,086 B2* | 10/2017 | Duggal | B63B 7/08 | |
| 10,058,808 B2* | 8/2018 | Haberkamp | B01D 39/163 | |
| 10,106,925 B2* | 10/2018 | Duggal | D04H 1/58 | |
| 10,391,434 B2* | 8/2019 | Haberkamp | B01D 39/163 | |
| 2002/0006502 A1* | 1/2002 | Nagaoka | D01F 8/12 | 428/374 |
| 2003/0118776 A1* | 6/2003 | Anderson | D01F 8/14 | 442/361 |
| 2003/0203695 A1* | 10/2003 | Polanco | D01F 1/10 | 442/361 |
| 2004/0266300 A1* | 12/2004 | Isele | D04H 13/02 | 442/327 |
| 2005/0032450 A1* | 2/2005 | Haggard | D01F 9/14 | 442/340 |
| 2005/0070866 A1* | 3/2005 | Isele | D04H 13/00 | 264/172.19 |
| 2006/0014460 A1* | 1/2006 | Alexander Isele | A61F 13/51401 | 442/85 |
| 2006/0057922 A1* | 3/2006 | Bond | D04H 3/16 | 442/341 |
| 2006/0084340 A1* | 4/2006 | Bond | D04H 13/02 | 442/351 |
| 2006/0292355 A1* | 12/2006 | Pourdeyhimi | D04H 1/49 | 428/212 |
| 2014/0148771 A1* | 5/2014 | Luce | A61F 5/448 | 604/345 |
| 2021/0307952 A1* | 10/2021 | Nielsen | A61F 5/448 | |
| 2023/0279590 A1* | 9/2023 | Buell | D04H 1/492 | |

* cited by examiner

COSMETIC SHEET MASKS FOR IMPROVED PRODUCT DELIVERY

FIELD OF THE INVENTION

The present invention relates to nonwoven fabrics, and their use as topical delivery systems for cosmetic and personal care products. More specifically, the invention pertains to sheet masks (including patches) made from non-woven fabrics.

BACKGROUND

Cosmetic and personal care sheet masks are popular for delivering a product to the face and other areas of the body. Typically, the suggested leave-on duration for a sheet mask is from 10 to 30 minutes. This time is required to allow a significant dose of product impregnated in the mask to transfer to the skin. Also, a user may experience a pleasant cooling sensation while the mask is on the skin. However, having to wear a sheet mask, such as a facial mask, for 10 to 30 minutes may be inconvenient for busy consumers who would benefit by getting the most from a sheet face mask in a much shorter amount of time. Furthermore, in general, the release rate of product from a conventional sheet mask does not match the absorption rate by the skin. When unabsorbed product is exposed to the ambient atmosphere, degradation, such as evaporative loss occurs. As a result of this, extra product is typically impregnated into the mask to make sure that a user will receive an adequate dose. This increases cost and waste. For these and other reasons, there remains a need for cosmetic sheet masks that can deliver a dose of aqueous product in significantly less than 10 minutes. The rate of release of an aqueous product from sheet fabric is largely dependent on the porosity of the fabric. In general, if fiber density and/or fiber size are reduced, then the porosity (and rate of release) will increase, but the integrity of a fabric made from these smaller fibers is compromised, and may not possess a requisite strength and durability. Therefore, one challenge addressed by the present invention is how to make a cosmetic sheet mask with increased and controllable rate of release, while still possessing the requisite strength and durability for mass production and distribution.

Different fabrics used in making cosmetic sheet masks have different fluid handling properties, such as the amount of fluid formulation that the fabric can hold, the rate of release into the skin and evaporative losses. These properties also depend on the arrangement of fibers (structure) within a given fabric. For example, cellulosic fabrics (such as cotton and rayon) can absorb as much as 8 times their mass, while a polyester (PET) fabric may only hold one or two times its mass. In cellulosic fabrics, fluid resides in the spaces (pores) between the fibers of the fabric, as well as in the pores of individual fibers. In the polyester fabric, fluid cannot penetrate into individual fibers, and only resides in the spaces (pores) between the fibers.

Another class of fabrics is nonwovens. Nonwovens are arrangements of fibers that are bonded together by entangling the fibers by any of several means, including mechanical, thermal and chemical. Nonwoven materials may be in the form of webs, mats, batts and sheets. The properties of the nonwoven material will depend, in part, on raw material selection, as well as the processes of web formation, bonding, and finishing. U.S. Pat. No. 3,338,992 is one example of an early effort to produce nonwoven webs from continuous synthetic fibers. A "fiber," as used herein, is a structure with a high aspect ratio (length/diameter). While there is not universal agreement, we use the definition of "microfiber" as a material with a diameter of about 0.5-5μ, and a linear mass density of less than 1 denier (den) (where denier is defined as the number of grams of fiber per 9000 meters). "Nanofibers", which we define as having a diameter of less than about 0.5μ, have a relatively high surface area-to-volume ratio, and high porosity compared to microfibers. By "microdenier" fibers, we mean fibers of less than 1 denier. "Staple fiber" refers to fibers of relatively short, definite length, whereas a "filament fiber" is a longer, effectively continuous fiber of very high aspect ratio.

A variety of techniques exists for producing the fibers that ultimately make up nonwoven fabrics. A "multicomponent fiber" is manufactured from two or more materials, such as different synthetic polymers. Fabrics made from multicomponent fibers benefit from having characteristics from each of the individual fiber components. Alternatively, after a multicomponent fiber is produced, it is sometimes useful to separate the component fibers from each other for individual processing. Micro-denier fibers are commonly produced this way. Common separating techniques may be classified as mechanical or solvent-based (such as: dissolving one type of fiber while leaving the other, or swelling the fibers to separate them).

"Bicomponent fibers" are comprised of two polymers of different chemical and physical properties. Typically, two polymers are co-extruded from the same spinneret to form a single filament, wherein the two polymers are delineated along a fine interface. The parameters necessary to successfully process two different starting materials in this fashion (for example: viscosities of the polymer fluids, drawability, compatibility with the spinning method) are known in the art. Several geometric arrangements of bicomponent fibers are common. Some of these are known in the field as side-by-side, segmented pie, segmented ribbon, segmented cross, tipped-trilobal, side-by-side bow-tie, core-sheath, and islands-in-the-sea. The present invention employs islands-in-the-sea fabrics that are made by specific techniques.

In general, island-in-the-sea fibers comprise numerous small filaments of one polymer (the islands) placed in a matrix of another polymer (the sea). U.S. Pat. No. 6,455,156 discloses one technique for making this kind of bicomponent fiber. However, in that process, an alkali solution must be used to dissolve the sea matrix in order to reach the island fibers (which are not adversely affected by the alkali solution). The use of non-environmentally friendly alkali solution is a drawback to this method, while also restricting the polymers that may be used for the island component to those that are not adversely affected by the alkali solution.

U.S. Pat. Nos. 7,981,226 and 8,420,556 (herein incorporated by reference, in their entirety) disclose a method of making high-strength, high surface area nonwoven fabrics from micro-denier, island-in-the-sea fibers, by fibrillating the bicomponent fibers. As a result, the island component is released from the sea matrix. In general, the sea component is sufficiently weak so that it can be fibrillated by hydroentangling, and the island and sea components must have little or no affinity for one another; that is, they must be incompatible. Incompatibility is defined as "two fiber components forming clear interfaces between the two such that one does not diffuse into the other." However, as explained in '226 and '556. "the critical feature of the invention is that the sea fibers are intertwined and entangled with the island fibers upon fibrillation. Consequently, while the island fibers can be manufactured at the micro and nano levels, the sea component also separates between the respective fibers forming micro and nano fibers of the sea component. Thus, the sea and island fibers produce continuous micro and nano fibers from a single bicomponent fiber. Also, with the fibers maintaining their structural integrity, they are enabled to intertwine and entangle amongst themselves forming the high strength fiber."

As further explained in U.S. Pat. Nos. 7,981,226 and 8,420,556, before fibrillation, the external fiber enwraps the internal fiber, and as a result, the internal fiber solidifies prior to the external fiber solidifying. This promotes an unusually strong island fiber, which can then be separated from the sea fiber by fibrillation or other external energy. In the process, both the internal island fibers and external sea fibers remain as continuous fibers, and bonds subsequently form between the various fibers. "This promotes the high strength aspect of the invention even though the respective fibers themselves are at the micro and nano levels."

U.S. Pat. Nos. 7,981,226 and 8,420,556 also disclose that it is preferable if the external energy for fibrillation is provided in the form of a hydroentanglement process by water-jetting. For this to work, both the internal island fibers and the external sea fibers must be insoluble in water. For this reason, PVA, a commonly used material in conventional island-in-the-sea fiber configurations, would not be useful if hydroentanglement is to be used or if the fibers will be used in fabrics for wet applications. Hydroentangling is usually performed with the bicomponent fibers on a web, and may result in micro-denier fibers of about 0.5 micron or less. Filament fibers produced in this manner may be incorporated into nonwoven fabrics that can be formed through spunbonding. Alternatively, staple fibers may be formed into a web and bonded by any one of several known means. The non-woven fabrics thus produced are said to be useful for making tents, parachutes, outdoor fabrics, house wrap, awnings, filters, wipes, cleaning cloths, and textiles. According to '226 and '556, the island fibers and sea fibers may comprise thermoplastic polymers, such as nylon 6, nylon 6/6, nylon 6,6/6, nylon 6/10, nylon 6/11, nylon 6/12, polypropylene, polyethylene, polyesters, co-polyesters, copolyetherester elastomers, polyolefins, polyacrylates, and thermoplastic liquid-crystalline polymers. Also, the thermoplastic polymer may comprise a copolyetherester elastomer with long chain ether ester units and short chain ester units joined head to tail through ester linkages.

To the best of our knowledge, nonwoven fabrics as described hereinafter, have never been used to produce cosmetic or personal care sheet masks with rapid release of product into the skin.

OBJECTS OF THE INVENTION

A main object of the present invention is a topical delivery system, such as a cosmetic or personal care sheet mask, with increased and controllable rate of release, while still possessing the requisite strength and durability for mass production and distribution.

Another object of the invention is to provide a topical delivery system, such as a cosmetic or personal care sheet mask, that can achieve adequate product delivery in ten minute or less, such as three to five minutes or less.

SUMMARY

We describe non-woven topical delivery systems, such as cosmetic or personal care sheet masks, for improved product delivery. These topical delivery systems comprise fabrics that are fashioned from micro-denier fibers that are produced by fibrillating bicomponent island-in-the-sea fibers. Fibrillation is performed by hydroentangling using jet strips with jet-to-jet spacing ranging from 600μ to 2400μ. The materials of the fibers and other relevant parameters are selected to provide a durable topical delivery system with controllable release rate of product.

DETAILED DESCRIPTION

We have discovered that certain fabrics made from micro-denier fibers are particularly useful in the area of topical delivery, especially cosmetic sheet masks, for improved product delivery. We describe a customized island-in-the-sea process to produce fabrics with certain defined parametric values. Particularly advantageous combinations of polymeric materials (island component/sea component) for the applications described herein include: polyamide 6/polylactic acid; polyamide 6/polyethylene; polypropylene/polylactic acid, although the invention is not limited to these combinations. In preferred embodiments of the invention the weight ratio of island component polymer to sea component polymer is between about 1:4 to about 1:6. For example, the island component polymer may make-up about 15-20% by weight of the bi-component fiber, while the sea component makes-up 80-85% by weight. Our observations are that masks made from such fabrics are the superior in terms of topical delivery of fluid products. This is particularly true when the step of hydroentangling is performed using a preferred jet-to-jet spacing. Preferred jet-to-jet spacing ranges from about 600μ-2400μ, with a water pressure of 10 bars to 1,000 bars If the jet-to-jet spacing is less than about 600μ, then the resulting fabric is too thin and too dense to release liquid product efficiently, so that a full dose of product may not be delivered in less than 10 minutes. On the other hand, if the jet spacing is greater than about 2400μ, then the fibers might separate so that the fabric loses mechanical integrity. With the preferred island-to-sea ratio and preferred jet-to-jet spacing, we have noticed a "sweet spot" where the fabric maintains mechanical integrity that is sufficient for the applications contemplated herein, while still being able to release liquid product efficiently. Fabrics produced within this sweet spot have a basis weight of about 30 g/m$^2$-100 g/m$^2$, preferably about 80 g/m$^2$-100 g/m$^2$. Nonwoven fabrics made according to the present invention also possess a unique "quilted" structure, which provides a visual differentiation from fabrics made by other methods.

Also important is fiber packing density (also known as solid volume fraction). Fiber packing density is the ratio of the volume occupied by the fibers to the volume of the fabric. Preferred fabrics of the present invention have a fiber packing density of about 5%-30%, which means that most of the sheet is empty space. Nevertheless, when all other parameters are as specified herein, the resulting fabric is sufficiently strong and durable for the applications contemplated herein.

When the application is a cosmetic sheet mask, for delivering a liquid composition to a skin surface, then the mask is impregnated with the liquid composition. Given the packing density specified above, the weight of liquid composition that may be impregnated into the mask typically ranges from 2 to 8 times the weight of the mask. At the same time, the specified packing density enables rapid transfer of product to a target surface. Thus, we are able to produce a cosmetic sheet mask that delivers a dose of product to a target surface in 3-5 minutes or less. As noted above, it is not uncommon that the suggested leave-on duration is 10 to 30 minutes, for cosmetic sheet masks currently on the market. That is the amount of time necessary to transfer a full dose of product to the skin surface. In contrast, we have discovered that a cosmetic sheet mask made from an island-in-the-sea nonwoven fabric, using the parameters specified herein, can achieve similar or superior results in 3-5 minutes, preferably in as little as 3 minutes, while achieving the requisite strength and durability for mass production, distribution and use of the mask.

Optionally, one or both of the island and sea components may be made from sustainable materials. Examples of useful sustainable materials include: polyvinyl alcohol, polybutylene succinate, recycled polyethylene, recycled polypropylene, recycled polyester or copolyester. Optionally, one or both of the island and sea components may be made from biobased materials, rather than fossil derived materials. Such materials include, for example, polyethylene derived from sugarcane, and polyamide derived from castor oil. Fabrics made from biobased materials, especially disposable items like cosmetic sheet masks, are better for the environment, and long term sustainability, in general.

Cosmetic sheet masks (including patches) according to the present invention may be made by impregnating the island-in-the-sea nonwoven fabric with one or more skin care formulations for treating the skin. In accordance with the packing density noted above, the total weight of the one or more formulations that may be impregnated into ta sheet mask typically ranges from 2 to 8 times the weight of the mask. Impregnating the sheet mask may be accomplished by any suitable means known in the art. Such cosmetic sheet masks may be used to treat various skin conditions. The sheet masks may be constructed to conform to a predetermined treatment area of the skin of a user, such as the face, neck, abdomen, or limbs or any portion thereof. For example, a full facial mask will typically extend from the hair line of the forehead to the chin, and from car to car, and be provided with apertures for the eyes, nose and mouth. Partial facial masks may be shaped to apply to the under eye area, or to the area lateral to the eyes, where crows feet develop, around the mouth where frown lines develop, or the T-zone of the nose. The exact size and shape of the cosmetic sheet will depend upon the intended use and product characteristics. The cosmetic sheets will have sufficient flexibility, and a size and shape adapted to conform to the desired treatment area of the user's skin. When the sheet masks are applied to and conformed to the contour of the skin, they can deliver to the skin a pre-determined dosage of one or more skin care formulations for treating the skin.

The formulation may comprise one or more skin benefit agents. Skin benefit agents may be selected from the group consisting of: anti-wrinkle or skin-tightening agents; anti-aging agents; moisturizing agents; skin whitening or depigmentation agents; anti-inflammatory agents; anti-acne agents; DNA repair agents; skin lipid barrier repair agents; anti-cellulite agents; wound-healing agents; stretch-mark/scar removing agents; plumping agents; hair growth retardation agents; hair growth stimulating agents; dark circle reduction or de-puffing agents; collagen synthesis or blood circulation enhancing agents; antioxidants; sebum-controlling agents; and pore-minimizing agents. The skin benefit agents may be either charged or neutral. Exemplary anti-wrinkle agents include, but are not limited to, acetyl hexapeptide-8, palmitoyl oligopeptide, dipeptide diaminobutyroyl, benzylamide diacetate, and the like. Exemplary skin-tightening agents include, but are not limited to, algae extract, pullulan, sweet almond seed extract, carbomer, palmitoyl oligopeptide, palmitoyl tetrapeptide-7, *Quercus suber* extract, and the like. Exemplary anti-aging agents include, but are not limited to, teprenone, trisodium resveratrol triphosphate, *Polygonum cuspidatum* root extract, whey protein, and the like. Exemplary moisturizing agents include, but are not limited to, hyaluronic acid, glycerin, urea, trehalose, and the like. Exemplary skin-whitening or depigmentation agents include, but are not limited to, ascorbic acid, magnesium ascorbyl phosphate, aminopropyl ascorbyl phosphate, mulberry root extract, *Scutellaria baicalensis* extract, grape extract, ferulic acid, hinokitol, and the like. Exemplary anti-inflammatory agents include, but are not limited to, spike moss extract, seal whip extract, *Polygonum cuspidatum* root extract, and the like. Exemplary anti-acne agents include, but are not limited to, salicylic acid, glycolic acid, lactobionic acid, and the like. Exemplary DNA repair agents include, but are not limited to, C1-C8 alkyl tetrahydroxycyclohexanoate, micrococcus lysate, bifida ferment lysate, and the like. Exemplary skin lipid barrier repair agents include, but are not limited to, phytosphingosine, linoleic acid, cholesterol, and the like. Exemplary anti-cellulite agents include, but are not limited to, *Coleus forskohlii* root extract, *Magnolia grandiflora* bark extract, *Nelubo nucifera* leaf extract, and the like. Exemplary wound-healing agents include, but are not limited to, *Mimosa tenuiflora* bark extract, soybean protein, and the like. Exemplary plumping agents include, but are not limited to, *Saccharomyces/xylinum* black tea ferment, *Anemarrhena asphodeloides* root extract, sodium hyaluronate, and the like. Exemplary hair growth retardation agents include, but are not limited to, ursolic acid, phytosphingosine, *Boswella serrata* extract, and the like. Exemplary hair growth stimulating agents include, but are not limited to, Serenoa *serrulata* fruit extract, licorice extract, acetyl glucosamine, and the like. Exemplary dark circle reduction or de-puffing agents include, but are not limited to, hesperidin methyl chalcone, dipeptide-2, *Passiflora incarnate* flower extract, linoleic acid, isolinoleic acid, and the like. Exemplary collagen synthesis or blood circulation enhancing agents include, but are not limited to, arginine, *Ascophyllum nodosum* extract, *Asparagopsis armata* extract, caffeine, and the like. Exemplary anti-oxidants include, but are not limited to, nordihydroguaiaretic acid, grape seed extract, green tea leaf extract, and the like.

We claim:

1. A sheet mask for delivering a liquid composition to a skin surface, the sheet mask comprising an island-in-the sea nonwoven fabric made from bicomponent island-in-the-sea fibers, wherein:
    the bicomponent island-in-the sea fibers comprise:
        an island fiber made from a first polymeric material;
        a sea fiber made from a second polymeric material;
    the weight ratio of the first polymeric material to the second polymeric material is between 1:4 and 1:6;
    the fiber packing density of the nonwoven fabric is 5%-30%; and
    the sea and island fibers are entangled by water-jetting with a jet-to-jet spacing of 600μ-2400μ.

2. An island-in-the sea nonwoven fabric according claim 1 wherein:
    the first polymeric material is polyamide 6 and the second polymeric material is polylactic acid, or
    the first polymeric material is polyamide 6 and the second polymeric material is polyethylene, or
    the first polymeric material is polypropylene and the second polymeric material is polylactic acid.

3. An island-in-the sea nonwoven fabric according claim 1 wherein:
    the first polymeric material, second polymeric material or both are selected from polyvinyl alcohol, polybutylene succinate, recycled polyethylene, recycled polypropylene, recycled polyester, copolyester, polyethylene derived from sugarcane, and polyamide derived from castor oil.

4. An island-in-the sea nonwoven fabric according claim 1 wherein the island and sea fibers are micro-denier fibers, and the basis weight of the fabric is 30 g/m$^2$-100 g/m$^2$.

5. A sheet mask according to claim 1, wherein the nonwoven fabric is constructed to conform to a predetermined treatment area of the skin of a user, such as the face, neck, abdomen, limbs or any portion thereof.

6. A sheet mask according to claim 5, wherein the weight of liquid composition in the nonwoven fabric is 2 to 8 times the weight of the nonwoven fabric.

7. A sheet mask according to claim 5 that is constructed as a full facial mask.

\* \* \* \* \*